United States Patent [19]

Sipos

[11] Patent Number: 5,302,400
[45] Date of Patent: Apr. 12, 1994

[54] PREPARATION OF GASTRIC ACID-RESISTANT MICROSPHERES CONTAINING DIGESTIVE ENZYMES AND BUFFERED-BILE ACIDS

[75] Inventor: Tibor Sipos, Lebanon, N.J.

[73] Assignee: Digestive Care Inc., Lebanon, N.J.

[21] Appl. No.: 901,758

[22] Filed: Jun. 22, 1992

[51] Int. Cl.$^5$ ................................. A61K 9/14
[52] U.S. Cl. ................... 424/494; 424/451; 424/497; 424/94.21; 424/94.6
[58] Field of Search ............ 435/186; 428/403; 523/210, 211; 424/94.21, 94.3, 94.6, 451, 461, 462, 470, 490, 494, 497

[56] References Cited

U.S. PATENT DOCUMENTS

| | | | |
|---|---|---|---|
| Re. 30,910 | 4/1982 | Weigand | 514/182 |
| 3,004,893 | 10/1961 | Martin | 167/73 |
| 4,079,125 | 3/1978 | Sipos | 424/480 |
| 4,280,971 | 7/1981 | Wischniewski et al. | 964/15 |
| 4,828,843 | 5/1989 | Pich et al. | 424/430 |
| 4,859,471 | 8/1989 | Fulberth et al. | 424/480 |
| 5,202,129 | 8/1993 | Samejima et al. | 424/489 |

FOREIGN PATENT DOCUMENTS 1296944 4/1971 France .
1362365 7/1970 United Kingdom .

*Primary Examiner*—Thurman K. Page
*Assistant Examiner*—Neil Levy

[57] ABSTRACT

Disclosed are gastric acid-resistant polymer-coated digestive enzymes/buffered-bile acid compositions, process for their preparations and methods of treating digestive disorders, impaired liver function, cystic fibrosis, regulating the absorption of dietary cholesterol, and for dissolving gallstones by administering said compositions to a mammal in need of such treatment.

10 Claims, No Drawings

PREPARATION OF GASTRIC ACID-RESISTANT MICROSPHERES CONTAINING DIGESTIVE ENZYMES AND BUFFERED-BILE ACIDS

BACKGROUND OF THE INVENTION

1. Field of the Invention

This invention relates to digestive enzymes and buffered composition of bile acids, and more particularly ursodeoxycholic acid, for ingestion by a mammal, a process for preparing said compositions, and a method for treating digestive disorders, impaired liver function, cystic fibrosis, regulating dietary cholesterol absorption and for dissolving gallstones by administering said compositions to a mammal in need of such treatment.

2. Reported Developments

It is known in the prior art that pancreatic enzymes administered to mammals can remedy enzyme deficiency caused by various diseased conditions of the pancreas, such as cystic fibrosis, pancreatitis, pancreatic enzyme deficiency and old age. Oral administration of compositions containing these enzymes require the presence of certain conditions in order for them to be safe and effective as will be described hereunder.

Pancreatic enzymes produced by the patient's pancreas are released into the duodenum, the pH of which is close to neutral or slightly alkaline. Under these pH conditions the enzymes are active and digestion of the food by the enzymes proceeds normally in the upper segment of the intestine. However, when pancreatic enzymes are administered exogenously to the patient, the gastric conditions in the stomach, namely the presence of acid and pepsin, will irreversibly inactive the enzymes. Therefore, orally administered enzymes must be protected against gastric inactivation so that they remain intact during their transit through the stomach into the duodenum.

Once the exogenously introduced enzymes reach the duodenum, another requirement must be satisfied: the enzymes must be released from their protective environment and intimately mixed with the food transferred from the stomach to effect digestion.

U.S. Pat. No. 4,079,125 incorporated herein by reference, addresses these requirements in a composition containing these enzymes and provides preparative methods for making the compositions. The compositions provided by said patent comprise: an enzyme concentrate in a binder selected from the group consisting of polyvinylpyrrolidone, microcrystalline cellulose, cellulose acetate phthalate, methylcellulose and alginic acid; a stabilizer selected from the group consisting of calcium carbonate, polyvinylpyrrolidone, cellulose acetate phthalate, methylcellulose, starch and modified starches and alginic acid; a disintegrant selected from the group consisting of citric acid, sodium carbonate, sodium bicarbonate, calcium carbonate, starch and modified starches and alginic acid; said mixture is coated with a non-porous, pharmaceutically acceptable enteric coating polymer which is insoluble in the pH range of from about 1.5 to about 5 normally present in gastric fluids, and soluble at a pH of from about 6 to about 9, the normal pH range for mammalian intestinal fluids.

The orally administered composition passes through the stomach while being protected against the acidic environment by its acid-insoluble coating which then disintegrates in the neutral to basic environment of the upper intestine releasing the enzymes from the composition. The process of making the compositions includes the provision of using a solvent and avoiding the presence of water in the blending step of the enzyme/binder/disintegrant, since it is believed that water deactivates some of the enzymes.

Contrary to the teaching of U.S. Pat. No. 4,079,125, it has now been discovered that the complete exclusion of the water (anhydrous condition) during the process of preparing the enzyme buffered composition of ursodeoxycholic acid (UDCA) in the form of microtablets and microspheres, leads to products that are extremely friable, tend to crumble into pieces upon drying in a fluidized bed dryer or conventional coating pan and disintegrates upon initiation of the polymer coating step. This results in large amounts of dust and agglomeration of the beads into multiplets during the process as well as improper doses of the enzyme/buffered-UDCA upon administration to the patient when quality control fails adequately to sort-out and discard said rejects.

It is also known that ursodeoxycholic acid (hereinafter UDCA or bile acid) is capable of augmenting liver function, dissolving gallstones and improving the nutritional state of patients having cystic fibrosis caused by hepatobiliary complications. See for example, Ursodeoxycholic Acid Dissolution of Gallstones in Cystic Fibrosis, Sahl, B., Howat, J., Webb, K., *Thorax*, 43:490-1 (1988); Effects of Ursodeoxycholic Acid Therapy for Liver Disease Associated with Cystic Fibrosis, Colombo, C., Setchell, K. D., Podda, M., Crosignani, A., Roda A., Curcio, L., Ronchi, M. and Giunta, A., *The Journal of Pediatrics*, 117:482-489 (1990); Effects of Ursodeoxycholic Acid Treatment on Nutrition and Liver Function in Patients with Cystic Fibrosis and Longstanding Cholestasis. Cotting, J., Lentze, M. J. and Reichen, J., *Gut* 31:918-921 (1990). Also, UDCA has recently gained acceptance as an effective therapeutic modality to dissolve small to medium size cholesterol gallstones in gallstone afflicted patients. See for example, The Effect of High and Low Doses of Ursodeoxycholic Acid on Gallstone Dissolution in Humans, Salen, G., Colalillo, A., Verga, D., Bagan, E., Tint, G. S. and Shefer, S., *Gastro.*, 78:1412-1418 (1980); Ursodeoxycholic Acid: A Clinical Trial of a Safe and Effective Agent for Dissolving Cholesterol Gallstones, Tint, G. S., Salen, G., Colalillo, A., Graber, D., Verga, D. Speck, J. and Shefer, S., *Annals of Internal Medicine*, 91:1007-1018 (1986); Clinical Perspective on the Treatment of Gallstones with Ursodeoxycholic Acid, Salen, G., *J. Clin. Gastroenterology*, 10 (Suppl. 2):S12-17 (1988); Nonsurgical Treatment of Gallstones, Salen, G. and Tint, G. S., *New England J. Med.*, 320:665-66 (1989); and Reducing Cholesterol Levels, Weigand, A. H., U.S. Pat. No. 3,859,437. The recommended dosage is 10 to 15 mg/kg of body weight. In some patients much higher dosage (for example, about 30 mg/kg of body weight) are required to achieve limited benefits. However, in some patients undesirable side effects (such as, severe diarrhea) seriously limit the use of this drug. The reasons for this wide variation of dosage requirements for therapeutic effectiveness and associated side effects are not completely understood. One hypothesis is that the free acidic form of UDCA is only partially neutralized in the upper intestine to its sodium salt form. The residual free acidic form of UDCA is poorly absorbed from the intestine, and a good portion of the administered dosage is excreted intact with feces. When a higher dosage of the acidic form of UDCA is administered to the patient, a large portion of it is neutralized in the distal parts of the intestine which in turn induces diarrhea, a highly undesirable side effect. Also, if the acidic form of UDCA is to be converted into its salt form in the duodenum, it will exhaust the buffering capacity of the duodenum and it will render the upper intestine partially acidic. The acidic pH impedes the function of the pancreatic enzymes and UDCA cannot emulsify fats and facilitate the hydrolysis of lipids. Furthermore, the many therapeutic benefits derived from the salt forms of UDCA cannot be realized. It should then follow, accordingly, that the salt forms of UDCA should be administered to patients in need of UDCA. U.S. Pat. No. 3,859,437 recommends the administration of a "small but effective amount sufficient to effect a reduction in the cholesterol level of said human being of the compound 3α 7β-dihydroxy-5β-cholanic acid (UDCA) and the non-toxic pharmaceutically acceptable salts thereof". However, administering the salt form of UDCA to patients has no advantage over the acidic form of UDCA and does not accomplish the desired results since the salt form of UDCA is converted back to the insoluble acidic form of UDCA by gastric acidity. Furthermore, the salt forms, i.e., sodium or potassium, of UDCA are extremely bitter-tasting, and in most patients cause esophageal reflux, nausea and vomiting. Because of these highly undesirable organoleptic and gastric side effects, the salt forms of UDCA has not gained therapeutic utility in the treatment of biliary diseases.

Pancreatic enzymes and salts of UDCA complement one another in the digestive system of a mammal. A dietary supplement containing both the enzymes and salts of UDCA would provide in a convenient predetermined dose the remedy needed to treat the above-described diseased states. However, the acidic form of UDCA is incompatible with pancreatic enzymes. Pancreatic enzymes/UDCA compositions have a pH of about 5 to 5.5. Under these acidic conditions most pancreatic enzymes show a low biological activity of about 10% to 40%. Lipase is especially affected by the low Ph for the reasons that: UDCA is only sparingly soluble in aqueous media and is inefficient to emulsify fats; and the acidic UDCA inactivates lipase since lipase requires a basic Ph for biological activity.

Pancreatic enzymes/UDCA containing compositions also lack sufficient shelf-life due to the denaturing and detergent effects of UDCA on the pancreatic enzymes. Because of these incompatibilities between UDCA and pancreatic enzymes the many benefits derivable from their combinations could not be realized by the prior art.

It has now been discovered that the problems associated individually with enteric coated microtablets and microspheres containing pancreatic enzymes and compositions containing UDCA, may be overcome in a dietary supplement containing both the pancreatic enzymes and a buffered UDCA composition. In accordance with the discovery, UDCA is micropulverized in the presence of a suitable buffer salt to obtain ultrafine particles that will readily dissolve in the intestinal juices under physiological conditions and provide a neutral to slightly alkaline media. The concentration of the buffer salt is adjusted to provide a 10% to 20% excess over what is required for the instant neutralization of UDCA.

Pancreatic enzymes then are combined with a micropulverized and buffered-UDCA and additionally buffered with a biologically compatible, pharmaceutically acceptable buffer that prevents deactivation of the enzymes and preserves the natural biological activities of both the enzymes and the buffered-UDCA. The pancreatic enzyme/buffered-UDCA composition can be prepared into microtablets and microspheres in the presence of moisture without inactivation of the enzyme/buffered UDCA composition thereby resulting in products that do not crumble upon drying or disintegrate upon initiation of the polymer coating procedure. The bitter taste and associated gastric disadvantages of UDCA is also eliminated by the polymer coating which prevents solubilization of the product in the mouth and stomach of the patient.

Still further, it has been discovered that microspheres in the range of 10 to 80 mesh size (about 2.0 to 0.177 mm range) can be prepared utilizing buffered-UDCA as seeds to build up the microspheres. Such small particle size microspheres are especially beneficial for use to treat pancreatic enzymes/UDCA deficiencies in cystic fibrosis children.

SUMMARY OF THE INVENTION

This invention will be described with particular reference to ursodeoxycholic acid, however, it is to be understood that other bile acids may be used as well.

In accordance with the present invention, digestive enzymes/buffered-UDCA compositions are provided which possess desirable characteristics heretofore absent in proposed or existing prior art products.

The digestive enzymes/buffered-UDCA is instantly soluble in water, while UDCA alone or in combination with a digestive enzyme is essentially insoluble.

Only the ionized or salt form of UDCA is absorbed from the intestine, while the acidic form of UDCA is insoluble and passes through the intestine intact, unless it is converted to the sodium salt by the intestinal buffers. However, many patients, such as patients with cystic fibrosis, pancreatitis, Billroth I & II diseases and some elderly people, are partially deficient in bicarbonate secretion and lack neutralization capacity to convert the acidic form of UDCA to the sodium salt of UDCA. These patients will only partially benefit from UDCA therapy. The buffered-UDCA containing composition of the present invention overcomes this problem by being instantly soluble in the intestinal juices and absorbable from the intestine. Additionally, the composition also provides extra buffering capacity to neutralize the acid chyme that is present in the intestine and greatly facilitates the efficient digestion of fats and lipids in the upper intestine.

The digestive enzyme/buffered-UDCA composition is microencapsulated and coated with an acid-resistant polymer-coating, which protects the composition from gastric acid and from conversion of the buffered-UDCA to the acidic form of UDCA. The polymer-coated microcapsules are tasteless and the problem associated with the offensive bitter taste of the uncoated acidic form of UDCA is thereby alleviated.

The microcapsules uniformly disperse with the food in the stomach and deliver high levels of biologically active digestive enzyme/buffered-UDCA into the duodenum. Once in the duodenum, the polymer coating dissolves within about 10 to 30 minutes and the enzyme/buffered-UDCA are released to enhance digestion of fats and lipids. The buffer salts readily dissolve in the intestinal juices and instantly neutralize the UDCA to the very soluble Na-UDCA. The soluble Na-UDCA emulsifies fats and accelerates digestion of triglycerides to readily absorbable fatty acids. As a result, the natural digestive conditions in the intestine are re-established. Epigastric pain, cramps, bloating, flatulence and stool frequency associated with maldigestion of fatty foods are reduced.

Salts of UDCA are absorbed more efficiently and in a greater quantity from the intestine than the insoluble acidic form of UDCA, resulting in a more efficient stimulation of the liver enzymes to conjugate ursodiol. The increased concentration of the conjugated ursodiol stimulates bile flow, enhances the displacement of toxic bile acid metabolites from the hepatocytes, decreases cholesterol secretion into bile, alters the cholesterol/phospholipid ratio of secreted bile and decreases the absorption of dietary cholesterol from the intestine. The overall result is decreased biliary cholesterol saturation, increased bile flow, dissolution of already formed cholesterol gallstones and protection of the liver from accumulated toxic metabolites.

The digestive enzymes/buffered-UDCA composition for the treatment of enzyme/UDCA deficient mammals comprises a blend of ingredients and a coating therefor expressed in weight per weight percentages based on the total weight of the composition:

a) from about 65 to about 90.0% of a concentrate of an enzyme selected from the group consisting of pancreatic proteases, lipases, nucleases and amylases;
b) from about 0.3 to about 13% of a micropulverized and buffered-UDCA in powder form, said buffer-/UDCA forming a mixture of a 1 to 1 neutralization equivalent ratio;
c) from about 0.8 to about 5% of a buffering agent selected from the group consisting of about 0.25 to about 5.0% sodium carbonate (anhydrous powder), sodium bicarbonate, potassium carbonate, potassium bicarbonate and ammonium carbonate and from about -.25 to about 1.5% tromethamine, diethanolamine and triethanolamine;
d) from about 0.5 to about 16% of a disintegrant selected from the group consisting of starch and modified starches, microcrystalline cellulose and propylene glycol alginate;
e) from about 3.0 to about 19% of an adhesive polymer selected from the group consisting of polyvinylpyrrolidone, hydroxypropyl cellulose, cellulose acetate phthalate and a 60:40 blend of ethyl cellulose and hydroxypropyl methyl cellulose; and
f) from about 7.0 to about 15% of a non-porous, pharmaceutically acceptable gastric acid-resistant polymer-coating which contains less than 2% talc and which is insoluble in the pH range of from about 1.5 to about 5 but is soluble in the pH range of from about 5.5 to about 9.

The digestive enzymes of the present invention includes Pancreatin of multiple strength, Pancrelipase, Trypsin, Chymotrypsin, Chymotrypsin B, Pancreatopeptidase, Carboxypeptidase A, Carboxypeptidase B, Glycerol Ester Hydrolase, Phospholipase A2, Sterol Ester Hydrolase, Ribonuclease, Deoxyribonuclease, α-Amylase, Papain, Chymopapain, Bromelain, Ficin, β-Amylase, Cellulase and β-Galactosidase (Lactase).

The micropulverized buffered-UDCA includes sodium, potassium and ammonium carbonates and bicarbonates, and tromethamine, ethanolamine, diethanolamine and triethanolamine salts or salt complexes.

In accordance with the present invention, the enzyme/buffered-UDCA composition is prepared by a process comprising the steps of:

a) micropulverizing a neutralizing equivalent of sodium carbonate (anhydrous) or other suitable buffering agent with a molar equivalent of UDCA in a centrifugal grinder or in an impact pulverizer;
b) blending dry, powdery ingredients selected from the group consisting of (i) from about 65 to about 90% w/w of an enzyme from the group consisting of pancreatic proteases, lipases, nucleases and amylases; (ii) from about 0.3 to about 13% w/w of a micronized buffered-UDCA from the group consisting of sodium carbonate, potassium carbonate, ammonium carbonate, tromethamine, ethanolamine, diethanolamine and triethanolamine; (iii) a buffering agent selected from the group consisting of from about 0.25 to about 5.0% w/w sodium carbonate (anhydrous), sodium bicarbonate, potassium carbonate, potassium bicarbonate and ammonium carbonate, and from about 0.25 to about 1.5% w/w, tromethamine, diethanolamine and triethanolamine; (iv) of from about 0.5 to about 8.0% w/w a disintegrant selected from the group consisting of starch and modified starches and microcrystalline cellulose and propylene glycol alginate; and (v) from about 3.0% to about 11% w/w of an adhesive polymer selected from the group consisting of polyvinylpyrrolidone, cellulose acetate phthalate, hydroxypropyl cellulose and methylcellulose;
c) wetting said blended ingredients with a liquid to cause the blend to stick together, wherein said liquid is selected from the group consisting of: 1%–25% w/w ethanol/75%–99% w/w 2-propanol/0.2%–2% w/w water; 98%–99% w/w 2-propanol/0.2%–2% w/w water; 1%–25% w/w methanol/0.2%–2% w/w water/75%–98% w/w 2 propanol/1%–5% w/w ethylacetate;
d) granulating or extruding the liquid-wetted blend through a 10 or a 18 mesh S/S screen;
e) converting the granules to a uniform diameter particle size;
f) compacting the uniform particles to spherical particles;
g) drying the spherical particles;
h) separating the spherical particles if not of uniform size according to desired sizes using U.S. Standard sieve screens;
i) coating the particles with a gastric acid-resistant polymer that dissolves under neutral or slightly basic conditions; and
j) drying the polymer-coated spherical particles.

DETAILED DESCRIPTION OF THE INVENTION

In preparing the pancreatic enzymes/buffered-UDCA containing microspheres of the present invention utilizing the extrusion, uni-sizer and marumerization process (later described) moisture must be included in the liquid or solvent-adhesive composition to render the adhesive polymer sticky enough to bind the enzymes/buffered-UDCA-containing fluffy powder into a pliable, solid mass. This prevents the crumbling of the microspheres during the drying and coating steps as well as allows the preparation of much smaller particle size microspheres, i.e. in the range of 10 to 80 mesh. Accordingly, it was found that the moisture level during the preparation of the composition should be in the range of from about 0.2% w/w to about 2.5% w/w, preferably, in the range of 0.2% w/w to 1.5% w/w, and most preferably in the range of 0.2% w/w to 1.0% w/w. When the compositions contained such amounts of moisture, the microspheres were found to be stable on aging and biological activity was preserved as long as the moisture level did not exceed about 2.5% w/w of the total composition.

Further reference is now made to the process of preparing compositions of the present invention.

The process for the manufacture of microspheres consists of:

1) Micropulverizing a neutralizing equivalent of sodium carbonate (anhydrous) or other suitable buffering agent with a molar equivalent of UDCA in a centrifugal grinder (Brinkman, Inc.) or in an impact pulverizer at a setting of 4 and employing a 0.2 μm screen.
2) Blending the micropulverized and dried, powdery ingredients together in a conventional blender and wetting the composition with a suitable liquid composition that causes the dry blend to stick together. The stickiness of the blend can be tested by compressing a handful of the blend in the palm of the hand. If the composition is compressible and sticks together but readily crumbles when squeezed between the fingers, sufficient liquid has been added to the composition for processing in the subsequent granulation step.
3) Granulating or extruding the liquid moistened composition through a 10 or a 18 mesh S/S screen using an oscillating/reciprocating granulator or a twin-screw extruder at a medium-to-high speed.
4) Classifying the granulated particles in a so-called "uni-sizer vessel" that rotates at 15 to 45 rpm for about 5 to 10 minutes. (The particles in the "uni-sizer vessel" are converted to a uniform diameter particle size.).
5) Compacting the uniform particles in a marumerizer, (a cylindrical vessel with a rotating disk at the bottom) for about 15 to 90 seconds. An alternative method of compacting the microspheres can also be achieved in a rotating conventional coating pan. In this case, the particles are tumbled in the pan for about 15 to 30 minutes, occasionally wetting the particles with a fine mist of the liquid composition. Larger microspheres are illustrated in Example V, prepared by employing the starting seeds of 40 to 60 mesh size of Step 5. The microspheres are wetted with the liquid polymer-containing mixture, followed by slowly dusting the buffered-UDCA/-buffer/disintegrant composition over the tumbling and flowing buffered-UDCA containing seeds. The sequence of these steps are repeated until the seeds are built up into microspheres having diameter in the range of 10 to 20 mesh, preferably 14 to 16 mesh.
6) Drying the spherical particles in an oven under a stream of warm and dry air not exceeding 35° C. and 40% relative humidity.
7) Separating the microspheres according to the desired sizes using U.S. Standard sieve screens.
8) Coating the desired and classified microspheres (for example, in the 14 to 16 mesh and separately in the 20 to 40 mesh size range) with an acid-resistant polymer in fluidized bed coating equipment. or in a conventional coating pan according to standard operating procedures as described in the manufacturer's instruction manual.
9) Drying the polymer coated microspheres in an oven under a stream of warm and dry air not exceeding 35° C. and 40% relative humidity until all the volatile substances (moisture and solvents) are removed.

The following examples will further serve to illustrate the compositions of the present invention wherein the compositions and the process of preparing them will be described with reference to microsphere forms; however, it is to be noted that the microtablet form of the composition and the process of making it is also intended to be covered by the present invention. The process of making the microtablet form of the composition is analogous to that of making the microspheres with the exception that the 40 to 80 mesh particles are compressed together into microtablets of 0.5 mm to 2.5 mm with a suitable tablet press and polymer coated, and should be understood by those skilled in the art.

EXAMPLE I

Generalized Formula Composition (polymer coated)

| Ingredients | % w/w |
| --- | --- |
| Disintegrant | 0.5–16 |
| Buffered-Bile acid (micronized) | 0.3–13 |
| Buffering agent (anhydrous) | 0.8–5 |
| Enzymes | 90.0–65 |
| Adhesive Polymer | 3.0–19 |
| Polymer coat/talc mixture | 7.0–15 |

EXAMPLE II

Formula Composition

| Ingredients | IIA (uncoated) % w/w | IIB (coated) % w/w |
| --- | --- | --- |
| Disintegrant | 6.0 | 5.2 |
| Buffered-Ursodeoxycholic acid (micronized) | 5.3 | 4.7 |
| Buffering agent (anhydrous) | 1.0 | 0.9 |
| Enzymes | 79.7 | 71.7 |
| Adhesive Polymer | 8.0 | 6.8 |
| Polymer coat/talc mixture |  | 10.7 |

EXAMPLE III

Formula Composition

| Ingredients | IIIA (uncoated) % w/w | IIIB (coated) % w/w |
| --- | --- | --- |
| Disintegrant | 3.0 | 2.7 |
| Sodium-carbonate-UDCA (micronized) | 5.3 | 4.7 |
| Buffering agent (anhydrous) | 1.0 | 0.9 |
| Enzymes | 82.3 | 72.8 |
| Adhesive Polymer | 8.4 | 8.2 |
| Polymer coat/talc mixture |  | 10.7 |

EXAMPLE IV

Formula Composition

| Ingredients | IVA (uncoated) % w/w | IVB (coated) % w/w |
| --- | --- | --- |
| Disintegrant | 2.0 | 1.8 |

-continued

| Ingredients | IVA (uncoated) % w/w | IVB (coated) % w/w |
|---|---|---|
| Potassium-carbonate-UDCA (micronized) | 2.5 | 2.3 |
| Buffering agent (anhydrous) | 2.0 | 1.8 |
| Enzymes | 86.5 | 79.3 |
| Adhesive Polymer | 7.0 | 6.5 |
| Polymer coat/talc mixture |  | 8.3 |

EXAMPLE V

Pancreatic Enzyme/Buffered-UDCA Microspheres

| Ingredients | % w/w |
|---|---|
| Buffered-UDCA starting seeds (20–40 mesh) | 8.8% |
| Disintegrant | 2.3% |
| Buffering agent (anhydrous) | 2.1% |
| Enzymes | 65.1% |
| Adhesive polymer mixture | 11.0 |
| Polymer coat/talc mixture | 10.7 |

The buffered-UDCA starting seeds in Example V were prepared as outlined in Example VI. Suitable bile acids and bile acid esters to prepare starting seeds in the particle size range of 20–60 mesh are: Ursodeoxycholic acid; ethyl and propyl esters of ursodeoxycholic acid; glycyl and tauroursodeoxycholic acid; N-methylglycyl ursodeoxycholate and N-methyl tauroursodeoxycholate.

TABLE I

Distribution of the Microspheres According to Sizes

| Mesh Size | (mm) | Example IIB Microspheres (%) | Example IIIB Microspheres (%) |
|---|---|---|---|
| 20 | 0.84 | 10.0 | 59.0 |
| 40 | 0.42 | 53.8 | 33.0 |
| 60 | 0.25 | 28.6 | 5.2 |
| 80 | 0.177 | 7.6 | 2.8 |

TABLE II

Moisture Content & Stability of the Microspheres

| | IIB | | IIIB | |
|---|---|---|---|---|
| Mesh Size | Moisture Content (%) | Stability (4 mo.)* | Moisture Content (%) | Stability (4 mo.)* |
| 20 | 1.1 | 99% | 1.6 | 98% |
| 40 | 0.9 | 98% | 1.9 | 96% |
| 60 | 0.8 | 100% | 2.5 | 95% |
| 80 | 0.9 | 98% | 2.7 | 85% |

*Lipase, Amylase and Protease Activities assayed according to USP XXII.

EXAMPLE VI

Preparation of Buffered-UDCA Starting Seeds

| | % w/w |
|---|---|
| Buffered-UDCA (micronized) | 60.7 |
| Disintegrant | 16.0 |
| Buffering agent | 4.6 |
| Adhesive polymer | 18.7 |

The process of making the buffered-UDCA-containing starting seeds consisted of: 1) micropulverizing the buffered-UDCA blend in a centrifugal grinder or an impact pulverizer, blending the resultant buffered-UDCA, disintegrant and the buffering agent together for 10-minutes; 2) spraying the composition with the adhesive polymer mixture until the powdery blend agglomerated; and 3) granulating or extruding the liquid moistened composition through a 10 or 18 mesh S/S screen using an oscillating/reciprocating granulator or a twin-screw extruder. The subsequent processing steps were the same as outlined in Steps (4) through (7) in the "Process of Manufacture for Microspheres".

Referring to ingredients used in the above examples:

Suitable Disintegrants in Examples I through VI are: Explotab (Mendell, Inc.), microcrystalline cellulose, and propylene glycol alginate (Kelco Co.)

Suitable Buffering Agents in Examples I through VI are: sodium carbonate (anhydrous), sodium bicarbonate, potassium carbonate, potassium bicarbonate, ammonium carbonate, tromethamine, diethanolamine and triethanolamine.

Suitable Enzymes in Examples I through VI are: Pancreatin, Pancrelipase and Pancreatin concentrates of high potency.

Suitable Bile Acids in Examples I through VI are: ursodeoxycholic acid, ethyl and propyl esters of ursodeoxycholic acid; glycyl and tauroursodeoxycholic acid; N-methylglycyl ursodeoxycholate and N-methyl taurineursodeoxycholate.

Suitable Adhesive Polymeric Agents in Example I through VI are: Hydroxypropyl cellulose (Klucel HF, Hercules Co.), polyvinylpyrrolidone (Plasdone, GAF Co.), a 60:40 blend of methyl cellulose and ethyl cellulose (Dow Chem. Co.), Hydroxypropyl methyl cellulose (Grades 50 and 55, Eastman Kodak Co.), cellulose acetate phthalate (Eastman Kodak Co.) and propylene glycol alginate (Kelco Co.).

Suitable Acid-Resistant Polymers to coat the microspheres in Example I through VI are: Hydroxypropyl methyl cellulose phthalate, Grades 50 and 55 (Eastman Kodak Co., or Shin-Etsu Chemical Co., Ltd.), Aquateric ® aqueous enteric coating polymer dispersion (FMC Corp.), Eudragit ® acrylic based polymeric dispersion (Rohm Pharma GMBH, Germany), and cellulose acetate phthalate (Eastman Kodak Co.).

Example VII will further illustrate the composition of the acid-resistant polymer-coating:

EXAMPLE VII

| | % w/w |
|---|---|
| Hydroxypropyl methyl cellulose phthalate* | 7.4 |
| Diethyl phthalate | 2.0 |
| 2-Propanol | 45.2 |
| Ethylacetate | 45.2 |
| Talc, USP | 0.2 |

*When the hydroxypropyl methyl cellulose phthalate was replaced with cellulose acetate phthalate an equally suitable acid-resistant polymer coating was obtained, as long as, talc was also included in the composition. The presence of talc with the film-forming polymer caused the deposition of an acid-impermeable polymer coat. In one modification of the coating procedure, the microspheres in Example III were first sealed of with an initial coat of CAP/DEP/TALC/solvent mix, followed by a secondary coating with an aqueous polymeric latex dispersion (for example, Aquateric ® or Eudragit ®). The employment of the initial CAP/DEP/TALC coating is important to seal off the microspheres and render them impervious to moisture. The advantage of using an aqueous based polymeric dispersion as the secondary coating is to save solvents that are evaporated during the solvent based coating step and cut down on environmental pollution.

The total amount of the composition required to be administered to an enzyme/bile salt deficient patient will vary with the severity of the conditions, age and other physical characteristics of the patient. The physicians will prescribe the total amount, the dosage and the frequency of dosage administration on a patient by patient basis. Generally, for enzyme/bile salt deficient patient from about 0.75 to about 1.5 grams of the composition are administered with each major meal, three times a day. Larger amount may, however, be required for certain conditions, such as for dissolving gallstones.

For ease of administration of the compositions it is preferred to use gelatin capsules containing about 0.2 to 0.5 grams microspheres or microtablets. Gelatin capsules which disintegrate in the acidic environment of the stomach are well-known and utilized in the prior art. Microtablets are of small size, having a diameter between about 1 to 5 mm and a thickness between 0.5 to 4 mm. The microtablet is prepared by conventional tableting procedure. However, the compositions of the present invention in the form of very small particle sizes may be used per se. The microspheres shown in Example IIB and IIIB (Table I) are in the 20 to 80 mesh size range and 92% of the polymer-coated particles were in the 20 to 40 mesh size range (0.42 to 0.25 mm). Young children or adults with certain diseases are unable to swallow big gelatin capsules. Microspheres of very small size of the present invention could then be administered to the patients with liquid food, such as milk, apple sauce and semi-solid foods.

What is claimed is:

1. A process for preparing a digestive enzyme/buffered-bile acid composition for the treatment of digestive enzymes/ursodeoxycholate deficient mammals comprising the steps of:
    a) blending dry, powdery ingredients selected from the group consisting of (i) from about 65 to about 90% w/w of an enzyme selected from the group consisting of pancreatic proteases, lipases, nucleases and amylase; (ii) from about 0.3 to about 13% w/w of a buffered micronized bile acid, said buffer selected from the group consisting of sodium and potassium carbonate and bicarbonate, ammonium carbonate, tromethamine, ethanolamine, diethanolamine and triethanolamine, said buffer/bile acid forming a mixture of a 1 to 1 neutralization equivalent ratio; (iii) a buffering agent selected from the group consisting of from about 0.25 to about 5.0% w/w sodium carbonate (anhydrous), sodium bicarbonate, potassium carbonate, potassium bicarbonate and ammonium carbonate, and from about 0.25 to about 1.5% w/w, tromethamine, diethanolamine and triethanolamine; (iv) of from about 3.0 to about 19% w/w of an adhesive polymer selected from the group consisting of polyvinylpyrrolidone, cellulose acetate phthalate, and a 60:40 blend of hydroxypropylmethyl cellulose, and ethyl cellulose; (v) of from about 0.5 to about 16% w/w a disintegrant selected from the group consisting of starch, modified starches, microcrystalline cellulose and propylene glycol alginate;
    b) wetting said blended ingredients with a liquid to cause the blend to stick together, wherein said liquid is selected from the group consisting of: 1%-25% w/w ethanol/75%-99% w/w 2-propanol/0.2%-2.5% w/w water; 98%-99% w/w 2-propanol/0.2%-2.0% w/w water; 1%-25% w/w methanol/0.2%-2.5% w/w water/75%-98% w/w 2 propanol/1%-5% w/w ethylacetate;
    c) granulating or extruding the liquid-wetted blend through a 10 or 18 mesh standard sleve screen;
    d) converting the granules to a uniform diameter particle size;
    e) compacting the uniform particles to spherical particles;
    f) drying the spherical particles under drying conditions not exceeding 35° C. and 40% relative humidity;
    g) separating the spherical particles if not of uniform size according to desired sizes using U.S. Standard sieve screens;
    h) coating the particles with from about 7.0 to about 15% of a gastric acid-resistant polymer that disintegrates under neutral or slightly basic conditions selected from the group consisting of hydroxypropyl methyl cellulose phthalate, cellulose acetate phthalate, an aqueous enteric coating polymer dispersion and an acrylic based polymeric dispersion; and
    i) drying the polymer-coated spherical particles under drying conditions not exceeding 35° C. and 40% relative humidity.

2. The process of claim 1 wherein said digestive enzyme is selected from the group consisting of Pancreatin, Pancrelipase, Trypsin, Chymotrypsin, Chymotrypsin B, Pancreatopeptidase, Carboxypeptidase A, Carboxypeptidase B, Glycerol Ester Hydrolase, Phospholipase A2, Sterol Ester Hydrolase, Ribonuclease, Deoxyribonuclease, α-Amylase, Papain, Chymopapain, Bromelain, Ficin, β-Amylase, Cellulase and β-Galactosidase.

3. The process of claim 1 wherein said composition is in the form of microspheres having a mesh size of about 10 to 80.

4. The process of claim 1 wherein said liquid for wetting the blended ingredient comprises from about 0.2% to about 2.5% moisture.

5. The process of claim 4 wherein said moisture content is from 0.2 to 1.5%.

6. The process of claim 5 wherein said moisture content is from 0.2 to 1.0%.

7. The digestive enzyme/buffered bile acid compositions for the treatment of digestive enzyme/ursodeoxycholic deficient mammals prepared by the process of claim 1.

8. A process for preparing a digestive enzyme/buffered-ursodeoxycholic acid composition for the treatment of digestive enzymes/ursodeoxycholic acid deficient mammals comprising the steps of:
    a) preparing a starting seed of the buffered-ursodeoxycholic acid comprising: micropulverizing the buffered-ursodeoxycholic acid in a centrifugal grinder or an impact pulverizer, blending the resultant micronized buffered-ursodeoxycholic acid with a disintegrant and a buffering agent;
    b) spraying said blend with a solution of the adhesive polymer until the blend agglomerates;
    c) granulating or extruding the liquid-wetted blend through a 10 or 18 mesh Standard Sleve screen;
    d) converting the granules to a uniform diameter particle size of 40 to 60 mesh;
    e) compacting the uniform particles to spherical particles;
    f) drying the spherical particles;
    g) separating the spherical particles if not of uniform size according to desired sizes using U.S. Standard sieve screens;
    h) using said 40 to 60 mesh particles as starting seeds for the preparation of larger microspheres; placing the 40-60 mesh starting seeds in a rotating coating pan, wetting the microspheres with the liquid- /adhesive polymer-containing mixture followed by slowly dusting the buffered-UDCA/buffer/disintegrant composition over the tumbling and flowing buffered-UDCA seed until the desired particles sizes are obtained;

i) coating the particles with a gastric acid-resistant polymer that dissolves under neutral or slightly basic conditions; and j) drying the polymer coated spherical particles.

9. The process of claim 8 wherein the particle size range of said starting seeds are from about 20 to about 60 mesh.

10. The process of claim 8 wherein said starting seed is selected from the group consisting of: sodium and potassium carbonate and bicarbonate, buffered-ursodeoxycholic acid; buffered-ethyl and propyl esters of ursodeoxycholic acid; sodium and potassium carbonate and bicarbonate blends of glycyl and tauroursodeoxycholic acid; buffered blends of N-methyl glycyl ursodeoxycholic acid and N-methyl tauroursodeoxycholic acid.

* * * * *